United States Patent [19]

Chapoteau et al.

[11] Patent Number: 5,814,521
[45] Date of Patent: Sep. 29, 1998

[54] METAL ION DETERMINATION BY SANDWICH AGGREGATION ASSAY

[75] Inventors: Eddy Chapoteau, Brooklyn; Jonathan Craine, Monsey; Bronislaw P. Czech, Peekskill, all of N.Y.; Anand Kumar, Pleasanton; Koon-wah Leong, Sunnyvale, both of Calif.

[73] Assignee: Bayer Corporation, Tarrytown, N.Y.

[21] Appl. No.: 703,982

[22] Filed: Aug. 28, 1996

Related U.S. Application Data

[60] Provisional application No. 60/005,137 Oct. 6, 1995.

[51] Int. Cl.$^6$ .................. G01N 33/20; G01N 35/546
[52] U.S. Cl. .................. 436/74; 436/79; 436/80; 436/81; 436/83; 436/84; 436/533; 436/534; 436/909
[58] Field of Search .................. 436/74, 534, 533, 436/909, 79, 80, 81, 83, 84

[56] References Cited

U.S. PATENT DOCUMENTS

| | | | |
|---|---|---|---|
| 4,080,171 | 3/1978 | Sano et al. | 23/253 TP |
| 5,407,831 | 4/1995 | Jing | 436/74 |
| 5,459,040 | 10/1995 | Hammock et al. | 435/77 |

FOREIGN PATENT DOCUMENTS

| | | |
|---|---|---|
| 0661267 | 7/1995 | European Pat. Off. . |
| WO8911475 | 11/1989 | WIPO . |
| WO9514926 | 6/1995 | WIPO . |

OTHER PUBLICATIONS

R. Schall et al., Clin. Chem., vol. 27, No. 7, pp. 1157–1164 (1981).
L. Bangs, Pure & Applied Chem., vol. 68, No. 10 pp. 1873–1879 (1996).
Aggarwal, et al., Clin. Chem. vol. 40, No. 8, pp. 1494–1502 (1994).
Schneider, et al., Analyst, vol. 118 pp. 993–936, (Sep. 1993).
Lerchi, et al., Anal. Chem. vol. 64 pp. 1534–1540, (1992).

Primary Examiner—Mary E. Ceperley
Attorney, Agent, or Firm—Rodman & Rodman

[57] ABSTRACT

The present invention relates to a method for the determination of polyvalent metal ions using a sandwich aggregation assay. One or more chelating agents capable of forming at least 2:1 or higher ratio stoichiometry complexes with polyvalent metal ions are attached to a suitable carrier such as latex particles through covalent bonds or by non-covalent interactions, such as hydophobic interactions. Upon complexation with the metal ions, the carriers of the complexing agent aggregate, causing an increase in light absorbance or light scattering which is proportional to the concentration of metal ions in the test sample. The measurement of the light absorbance or light scattering by a suitable instrument, such as a spectrophotometer or nephelometer provides a means for measuring the concentration of metal ions.

44 Claims, 2 Drawing Sheets

METAL ION DETERMINATION BY SANDWICH AGGREGATION ASSAY

This application claims the benefit of U.S. Provisional Application No. 60/005,137 filed Oct. 6, 1995.

BACKGROUND OF THE INVENTION

1. Field of the Invention

The invention relates to a novel method and reagents for the measurement of polyvalent metal ions in aqueous media, in particular, lead ions in physiological fluids.

2. Description of Related Art

Heavy metals, such as lead, cadmium, mercury, etc., are know to be toxic and to have deleterious effects on humans. Lead and its compounds, which over the centuries have been widely distributed in the environment as a result of their industrial uses, pose a significant health hazard. Lead toxicity is due to its affinity to thiol and cellular phosphate groups of enzymes and proteins. It also inhibits biosynthesis of heme and increases premature red cell destruction. Lead is toxic to the central nervous system, especially in children. It is estimated that over 3 million preschool children have dangerously elevated lead concentrations. While the largest part of environmental lead results from the combustion of leaded gasoline, the most concentrated source of lead in the environment of children is lead-containing paint. Lead uptake can occur throughout the gastrointestinal tract, lungs, or skin. It accumulates in bones, kidneys, liver and other organs. In addition to exhibiting neurotoxicity, lead has also been classified as a probable carcinogen.

The determination of lead in whole blood is important for monitoring exposure, particularly in children. In 1991, the Centers for Disease Control and Prevention in the United States lowered the acceptable limit of blood lead concentration from 25 $\mu$g/dL to 10 $\mu$g/dL and recommended screening for blood lead of all children under the age of six. Thus, the popular indirect method of lead determination by the fluorescence of zinc protoporphyrin became unsuitable due to its inadequate sensitivity. The measurement of lead in whole blood at concentrations below 20 $\mu$g/dL poses a challenge due to the complex nature of the matrix. A simple, reliable, and inexpensive method of measuring lead in blood is not available. Atomic absorption spectrophotometry and anodic stripping voltametry are the most commonly used methods. Although they are claimed to be accurate, they are also cumbersome to use, susceptible to contamination, and costly.

Other methods of lead determination have recently been reported. Use of stable isotope dilution gas chromatography-mass spectrometry (Aggarwal, et al. *Clinical Chemistry*, vol. 40, no. 8, pp. 1494–1502 (1994) for the determination of lead in urine and whole blood has been described. Spectrophotometric determination of lead in water using a porphyrin system has been reported (Schneider, et al. *Analyst*, vol. 118, pp. 933–936 (July 1993). Also, measurement of lead by a lead-selective optode, with subnanomolar detection limit, has been demonstrated (Lerchi, et al. *Analytical Chemistry*, vol. 64, no. 14, pp. 1534–1540 (July 1992). Enzyme-based biodetection systems for lead, which employ δ-aminolevulinic acid dehydrase (Silbergeld, U.S. Pat. No. 5,354,652 of Oct. 11, 1994) or isocitrate dehydrogenase (Henkens et al., U.S. Pat. No. 5,217,534 of Jun. 8, 1993) have also been proposed.

SUMMARY OF THE INVENTION

The present invention relates to a method for the determination of polyvalent metal ions using a sandwich aggregation assay. One or more chelating agents capable of forming at least 2:1 or higher ratio stoichiometry complexes with polyvalent metal ions are attached to a suitable carrier such as latex particles through covalent bonds or by non-covalent interactions, such as hydrophobic interactions. Upon complexation with the metal ions, the carriers of the complexing agent aggregate, causing an increase in light absorbance or light scattering which is proportional to the concentration of metal ions in the test sample. The measurement of the light absorbance or light scattering by a suitable instrument, such as a spectrophotometer or nephelometer provides a means for measuring the concentration of metal ions.

DESCRIPTION OF THE PREFERRED EMBODIMENTS

Figure 1:
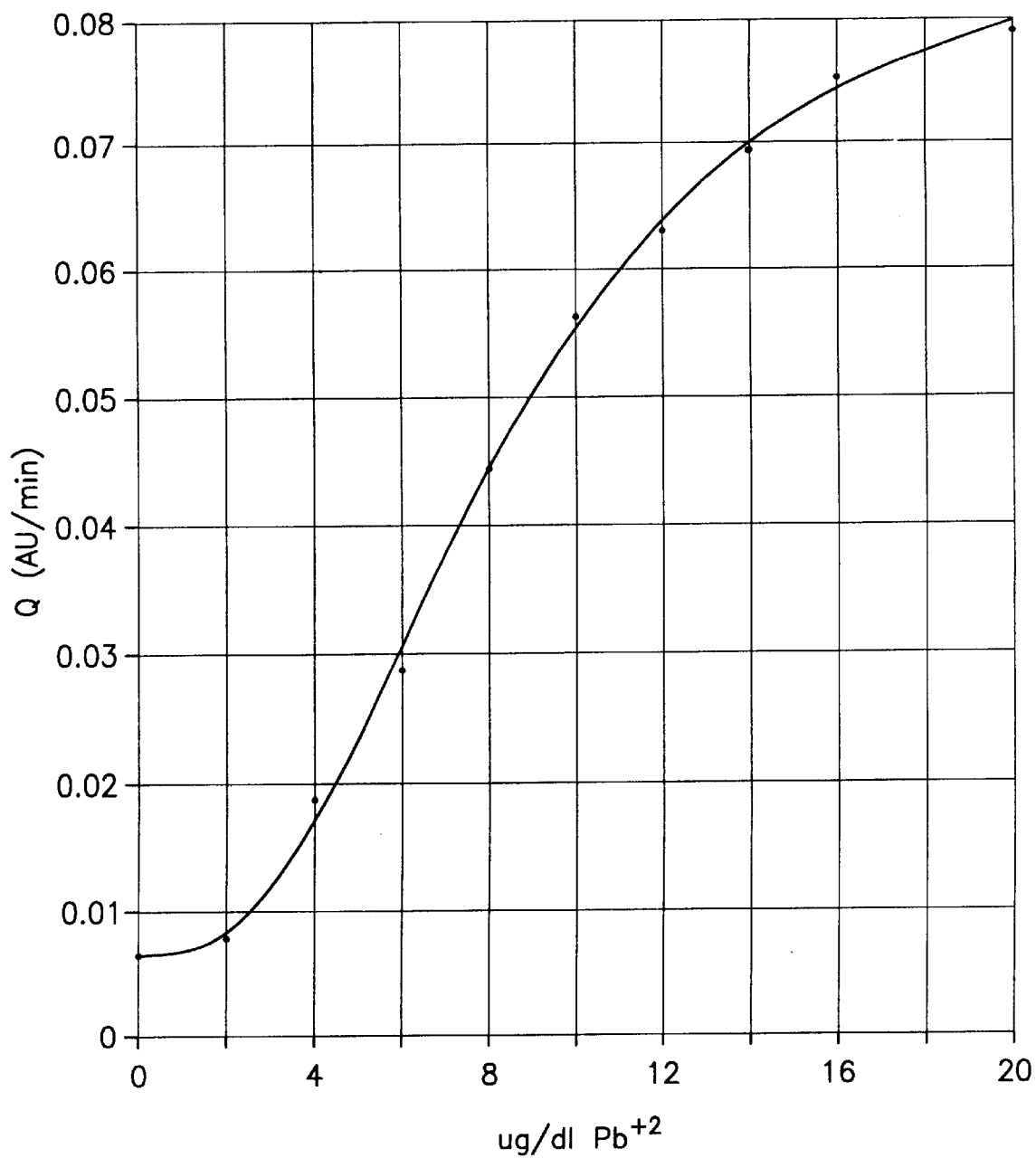

The present invention can be used to detect and measure a variety of metal ions including lead, copper, cadmium, cobalt, calcium, chromium, iron, aluminum, manganese, molybdenum, mercury, nickel, uranium, vanadium, zinc, magnesium, and the like. The sensitivity and selectivity of the system comprising a chelating agent associated with a carrier will depend on the chelating agent used. Furthermore, selectivity can be enhanced by using suitable masks, such as neocuproine to mask copper. The metal ions are most often found in a matrix, such as water, blood, urine, serum, milk and the like.

Chelating agents which form complexes, for example with lead, can be selected from, but are not limited to, a variety of compounds such as mercaptoamides, mercaptothioamides, mercaptans, mercaptoamines, mercaptothiones, aminothiones, thiohydroxamic acids, hydroxypyridinethiones, aminothiophenols, aminophenols, and dithiocarbamates.

The chelating agent can be bound or linked to a suitable carrier at the time of formation of the reaction mixture, or it can be in a form capable of becoming linked to the carrier. In the latter instance, for example, an interaction between a ligand and a specific binding partner for the ligand, such as antibody-antigen, hapten-anti-hapten antibodies, or avidin-biotin can be utilized. The binding partner can be attached to the carrier, either by covalent or non-covalent means.

A conjugate which comprises the ligand and the chelating agent which forms at least a 2:1 or higher ratio stoichiometry complex with the metal ion can be prepared. For all practical purposes the maximum ratio is controlled by the valence of the metal. Thus, most ratios of conjugate to metal ion will vary from 2 to 3:1. Upon contact with the metal ions, the conjugate forms a complex which, in turn, induces aggregation of the carrier due to the ligand-binding partner interaction.

The carrier can be soluble or insoluble in the reaction mixture as long as aggregation of the carrier results in a measurable change in light absorbance or light scattering. The carrier is typically particulate matter, and can be a microparticle such as latex particles made by emulsion or suspension polymerization, fine pigments, particles of oxides, for example, silicon oxide, titanium oxide or zinc oxide, and sulfates such as barium sulfate or calcium sulfate.

The microparticle can also be neutral or synthetic macromolecules, for example, polysaccharides, certain polypeptides or dendrimers. The macromolecule can be linear, globular or crosslinked. The microparticles can have a mean diameter within the range of from about 0.001 microns to about 10 microns, preferably about 0.01 to about 1 micron, and most preferably about 0.1 to about 0.25 microns. The only restriction in the microparticle of choice is that it should not contain ions which will interfere with the specific chelating reaction or specific metal detection.

In a preferred embodiment, a conjugate comprising biotin and thiolactic acid linked together by a polyether linker is contacted with a sample containing lead. A 2:1 conjugate/lead complex is formed. The complex is then contacted with latex particles coated with avidin. Due to high affinity of biotin toward avidin, aggregation occurs, and an increase in absorbance, which is proportional to the concentration of lead and is measured with a suitable analytical device, such as a spectrophotometer.

The following examples set forth various aspects of the subject invention. It will be understood that the formulations and procedures which follow are provided for purposes of illustration only and that other equivalent ingredients, proportions, and procedures can be employed in accordance with the principles of this invention.

EXAMPLE 1

Preparation of Reagent 1 for Lead Determination

A stock solution (2.0 mL) of 2.5 mg/mL (2-phenyl)ethyl thiolactic acid amide in ethanol was prepared. An aliquot (8 µL) of this solution was added to 10 mL of 0.01N NaOH and stirred. To this solution was added 0.5 mL of 5% polyvinyltoluene latex and the mixture was stirred for 2 hours to form the reagent 1 composition.

EXAMPLE 2

Determination of Lead with Reagent 1

A sample of reagent 1 (0.30 mL) was mixed with 1.7 mL of 0.1M 2-amino-2-methylpropanol (AMP) buffer (pH 10) containing 0.1N NaCl, in a 3 mL cuvette. A 10 µL sample of an aqueous solution of lead nitrate ($1.0 \times 10^{-5}$M) was added to obtain $5.0 \times 10^{-8}$M $Pb^{2+}$ in the cuvette, mixed, and the change in absorbance at 600 nanometers (nm) was recorded after 5 minutes with a Cary 3 spectrophotometer (Varian Analytical Instruments). Other concentrations were obtained by adding 2, 5 and 10 µL of $1.0 \times 10^{-4}$M lead nitrate to obtain [$Pb^{2+}$] concentrations of 1.0, 2.5, and $5.0 \times 10^{-7}$M, respectively. Table 1 shows the lead response data obtained from the spectrophotometer:

TABLE 1

| [$Pb^{2+}$], M | $\Delta A_{600}$(5 min.) |
|---|---|
| 0 | 0.044 |
| $5.0 \times 10^{-8}$ | 0.107 |
| $1.0 \times 10^{-7}$ | 0.170 |
| $2.5 \times 10^{-7}$ | 0.440 |
| $5.0 \times 10^{-7}$ | 0.540 |

EXAMPLE 3

Preparation of Reagent 2 for Lead Determination

A stock solution (2.0 mL) of 2.5 mg/mL (2-phenyl)ethyl amide of N-(2-mercaptopriopionyl)glycine in ethanol was prepared. An aliquot (20 µL) of this solution was added to 10 mL of 0.01N NaOH and stirred. To this solution, 0.5 mL of 5% polyvinyltoluene latex was added and the mixture was stirred for 2 hours to form the reagent 2 composition.

EXAMPLE 4

Table 2 Shows Lead Response Data Obtained with Reagent 2 Using the Procedure of Example 2.

TABLE 2

| [$Pb^{2+}$], M | $\Delta A_{600}$(5 min.) |
|---|---|
| 0 | 0.120 |
| $5.0 \times 10^{-8}$ | 0.260 |
| $1.0 \times 10^{-7}$ | 0.313 |
| $2.5 \times 10^{-7}$ | 0.775 |
| $5.0 \times 10^{-7}$ | 0.870 |

EXAMPLE 5

Lead Assay

A sample of reagent 2 (0.30 mL) was mixed with 1.3 mL of 0.14M 2-amino-2-methylpropanol (AMP) buffer (pH 10) containing 0.13N NaCl, in a 3 mL cuvette. A 0.4 mL sample of an aqueous solution of lead nitrate (0, 10, 15, 20, 30 & 50 µg/dL $Pb^{2+}$) was added to the buffer in cuvette, mixed, and the absorbance at 600 nm was recorded after 5 minutes with a spectrophotometer. A sample of lead responses is shown in Table 3.

TABLE 3

| [$Pb^{2+}$], µg/dL | $A_{600}$(5 min.) |
|---|---|
| 0.0 | 0.855 |
| 10.0 | 0.912 |
| 15.0 | 0.996 |
| 20.0 | 1.135 |
| 30.0 | 1.272 |
| 50.0 | 1.452 |

The lead level in the data shown in Table 3 is comparable to toxic concentrations of lead found in blood in cases of lead poisoning.

EXAMPLE 6

Preparation of Reagent 3 for Calcium Determination

A stock solution (2.0 mL) of didecylphosphate in ethanol was prepared. An aliquot (0.10 mL) was added to 10 mL of 0.01N NaOH and stirred. To this solution was added 0.5 mL of 5% polyvinyltoluene latex and the mixture was stirred for 2 hours to form the reagent 3 composition.

EXAMPLE 7

Determination of Calcium with Reagent 3

A sample of reagent 3 (0.30 mL) was mixed with 1.7 mL of 0.2N NaOH in a 3 mL cuvette. Samples (5–10 µL) of an aqueous solution of calcium chloride (0.1M) were added, mixed, and the change in absorbance at 600 nm was recorded with a Cary spectrophotometer after 5 minutes. Responses to different calcium levels are shown in Table 4.

TABLE 4

| [$Ca^{2+}$], M | $\Delta A_{600}$(5 min.) |
|---|---|
| 0 | 0 |
| $2.5 \times 10^{-4}$ | 0.120 |
| $3.5 \times 10^{-4}$ | 0.220 |
| $5.0 \times 10^{-4}$ | 0.660 |

In the preparation of chelating agents used in reagents for lead determination, unless specified otherwise, reagent grade reactants and solvents were used as received from chemical suppliers. Dimethylsulfoxide (DMSO) was dried over molecular sieves (4Å)(Aldrich). 1,17-diamino-3,6,9,12,15-pentaoxa-heptadecane was synthesized according to a published general procedure (Lehn, Tetrahedron 29, 1629, 1979). Melting points were determined on a Thomas-Hoover capillary apparatus. $^1$H NMR spectra were recorded with a Varian Gemini 200 MHz spectrometer and chemical shifts are reported in parts per million (δ) downfield from tetramethylsilane.

EXAMPLE 8

Preparation of N-(2'-phenylethyl)-2-mercaptopropanamide

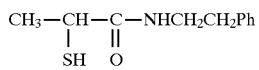

N-hydroxysuccinimide (0.58 g, 5.0 mmol) and dicyclohexylcarbodiimide (1.03 g, 5.0 mmol) was added to a solution of thiolactic acid (0.53 g, 5.0 mmol) in $CH_2Cl_2$ (8 mL). The mixture was stirred overnight at room temperature and filtered into 2-phenethylamine (0.61 g, 5.0 mmol). The reaction mixture was stirred for 24 hours at room temperature, filtered, and the solvent was removed in vacuo from the filtrate. The residue was chromatographed on silica gel with $CH_2Cl_2$ and $CH_2Cl_2$/MeOH (98/2) as eluent to give 0.68 g (65%) of the N-(2'-phenylethyl)-2-mercaptopropanamide product as a solid with mp 78°–79° C. $^1$H NMR(CDCl$_3$): δ1.51 (d, 3H), 1.93 (d, 1H), 2.84 (t, 2H), 3.30–3.60 (m, 3H), 6.90 (br s, 1H), 7.15–7.38 (m, 5H).

EXAMPLE 9

Preparation of N-(2-phenylethyl)amide of 2-mercaptopropionylglycine

N-hydroxysuccinimide (0.58g, 5.0 mmol) and dicyclohexylcarbodiimide (1.03 g, 5.0 mmol) was added to a solution of 2-mercaptopropionylglycine (0.82 g, 5.0 mmol) in DMSO (16 mL) and the mixture was stirred for 5 hours at room temperature. The mixture was filtered into 2-phenethylamine (0.60 grams, 5.0 mmol) and stirred overnight at room temperature. The solvent was removed in vacuo and the residue was column chromatographed on silica gel with CHCl$_3$/MeOH (97/3) as eluent to give 0.55 g (41%) of the product as a solid with mp 116°–118.5° C. $^1$H NMR (CDCl$_3$): δ1.51 (d, 3H), 2.02 (d, 1H), 2.81 (t, 2H), 3.33–3.60 (m, 3H), 3.86 (d, 2H), 6.29 (br s, 1H), 7.10–7.37 (m, 5H).

EXAMPLE 10

Preparation of Biotin-Thiolactic Acid Conjugate

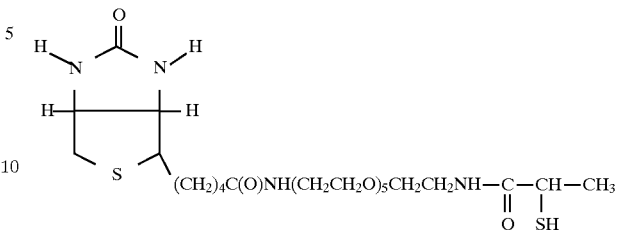

A solution of di-tert-butyl dicarbonate (0.78 g, 3.57 mmol) in ethyl ether (10 mL) was added dropwise, over a 3 hour period, to a solution of 1,17-diamino-3,6,9,12,15-pentaoxaheptadecane (2.00 g, 7.1 mmol) in DMSO (10 mL) at 16°–20° C. The reaction mixture was stirred at room temperature for 24 hours. A sufficient amount of water and ethyl ether were added to partition the reaction mixture. The organic layer and aqueous layer was separated. The aqueous layer was extracted first with ethyl ether and then with $CH_2Cl_2$. The organic layers were combined and dried over $K_2CO_3$. The solvent was removed in vacuo and the residue was column chromatographed on deactivated basic alumina with CHCl$_3$/MeOH (98/2) to give 0.90 g (33%) of the mono-BOC-protected product $NH_2(CH_2CH_2O)_5CH_2CH_2NH$-BOC as a pale-yellow, viscous liquid. $^1$H NMR (CDC$_3$+D$_2$O): δ1.41 (s, 9H), 2.82 (br s, 2H), 3.28 (t, 2H), 3.45–3.67 (m, 22H).

N-hydroxysuccinimide (0.12 g, 1.04 mmol) and dicyclohexyldiimide (0.21 g, 1.02 mmol) was added to a solution of biotin (0.24 g, 0.98 mmol) in DMSO (2 mL). The mixture was stirred overnight at room temperature and filtered into t-butoxycarbonyl (BOC) protected amine $NH_2(CH_2CH_2O)_5CH_2CH_2NH$-BOC (0.35 g, 0.96 mmol). The reaction mixture was stirred at room temperature for. 20 hours. The solvent was removed in vacuo and the residue was column chromatographed on silica gel with CHCl$_3$/MeOH (9/1) as eluent to give 0.60 g (~100%) of biotin derivative

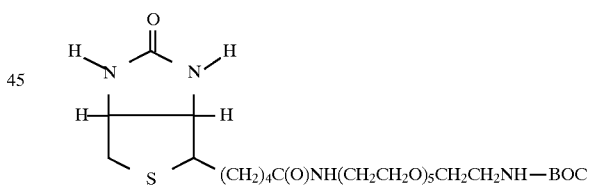

as a gelatinous solid. $^1$H NMR (CDCl$_3$): δ1.43 (s, 9H), 1.57–1.82 (m, 6H), 2.22 (t, 2H), 2.67–2.97 (m, 2H), 3.07–3.68 (m, 25H), 4.26–4.35 (m, 1H), 4.45–4.54 (m, 1H), 5.10 (br s, 1H), 5.38 (br s, 1H), 6.32 (br s, 1H), 6.32 (br s, 1H), 6.70 (br s, 1H).

The biotin derivative was treated with trifluoroacetic acid (10 mL) and the solution was kept at room temperature for 0.5 hours. The solvent was removed in vacuo and the residue was dissolved in dimethyl formamide (2 mL) and made basic with triethylamine. To this solution was added 1 mmol of N-hydroxysuccinimide ester of thiolactic acid. The mixture was stirred overnight at room temperature. The solvent was removed in vacuo, the residue was redissolved in CHCl$_3$ and washed with deoxygenated water to prevent oxidation of sulfhydryl groups. The solvent was removed in vacuo and the residue was column chromatographed on silica gel with CHCl$_3$/MeOH (9/1→8/1) to produce the conjugate,

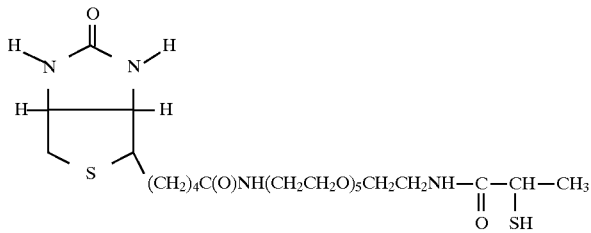

(CH₂)₄C(O)NH(CH₂CH₂O)₅CH₂CH₂NH—C—CH—CH₃
                                ‖   |
                                O   SH $^1$H NMR (CDCl$_3$+D$_2$O): δ1.37–1.95 (m, 10H), 2.23 (t, 2H), 2.61–2.97 (m, 3H), 3.16 (q, 1H), 3.37–3.72 (m, 24H), 4.28 (m, 1H), 4.45–4.55 (m, 1H).

EXAMPLE 11

Preparation of Avidin Latex Particles (60 μg/mg)

4.0 ml of 5.0% (w/v) 165 nm core-shell latex particles made of a polyvinyltoluene core and a polyvinylbenzylchloride shell were prepared in accordance with U.S. patent application Ser. No. 08/330,259 filed Oct. 27, 1994, and incorporated by reference herein. The core-shell latex particles were added to 15.0 ml 0.01M phosphate buffer pH 9.5 and stirred for 30 minutes. 20 ml 0.01M phosphate buffer pH 9.5 containing 12.0 mg avidin were then added and stirred an additional 30 minutes. The suspension was incubated at 40° C. for 3 hours in an incubator equipped with a mechanical shaker. After 3 hours the suspension was removed from the incubator, 5.0 ml of 2M ethanolamine added, and the mixture incubated an additional 18 hours at 40° C. Equal volumes of the suspension were added to 2 tubes and centrifuged at 16,000 rpm for one hour at a temperature in the range of 8°–15° C. in a refrigerated ultracentrifuge. The supernatant was discarded and 10.0 ml solution of 0.9% (w/v) NaCl, 0.02% (w/v) Tween-20 added to the pellet in each tube, sonicated and centrifuged at 16,000 rpm. The resuspension, sonication and centrifugation steps were repeated twice with 10 ml aliquots of NaCl solution. The pellets were then combined and resuspended in 100 ml solution of 0.9% (w/v) NaCl, 0.2% Tween-20, and 0.5 mM NaOH. This solution was then sonicated to obtain a uniform avidin latex suspension. The avidin particles were stored at 4° C.

EXAMPLE 12

Determination of Lead Using Biotin Thiolactic Acid Conjugate (Reagent 4)

A stock solution of 5.0×10$^{-5}$M biotin thiolactic acid conjugate was prepared in methanol containing 0.05% v/v tributylphosphine. An aliquot (40 μl) of this solution was added to 2.0 ml of 0.2N NaCl, 0.05% Triton X-100 (Rohm and Haas) and stirred to form R1. R2 consisted of a 2 mg/ml solution of 60 μg/mg avidin latex particles (Example 11) in 0.9% (w/v) NaCl, and 0.1% (w/v) Triton X-100.

The assay of lead was done on an RA-XT analyzer (Bayer Corporation, Tarrytown, N.Y., USA) at 37° C. using zero-order quadratic rate chemistry parameters. RA-XT parameters:

R1 320 μl
R2 80 μl
Sample volume 4 μl
Filter 600 nm
Delay time 15 seconds
R2 delay 1 minute Aqueous lead samples were prepared to contain 0.0–0.1 mM lead. The samples were diluted 1:100 on the instrument to yield final concentrations of 0–20 μg/dl. The quadratic rate (Q) in (AU/min) reported by the instrument is tabulated in Table 5 and was used to construct the response curve shown in FIG. 1.

TABLE 5

Lead response on RAXT

| [Pb$^{2+}$], μg/dl | Q(AU/min) |
|---|---|
| 0 | 0.006 |
| 2.0 | 0.008 |
| 4.0 | 0.0185 |
| 6.0 | 0.029 |
| 8.0 | 0.0436 |
| 10.0 | 0.0562 |
| 12.0 | 0.063 |
| 14.0 | 0.0696 |
| 16.0 | 0.0756 |
| 20.0 | 0.0794 |

As a control experiment, the lead response was also determined in the absence of the biotin conjugate. Example 12 was repeated without addition of biotin thiolactic acid conjugate to show that the agglutination was due to the formation of the 2:1 complex and not to the non-specific agglutination of the avidin latex particles by the divalent cation. The results appear in Table 6.

TABLE 6

Lead response of avidin latex particle

| [Pb$^{2+}$], μg/dl | Q(AU/min) |
|---|---|
| 0 | 0.0023 |
| 20.0 | 0.0032 |

EXAMPLE 13

Preparation of Chelating Agent (Reagent 5) Used in Copper Determination

N-hydroxysuccinimide (0.24g, 2.08 mmol) and dicyclohexylcarbodiimide (0.42 g, 2.04 mmol) was added to a solution of biotin (0.50 g, 2.05 mmol) in DMSO (5.5 mL). The mixture was stirred for 5 hours at room temperature and filtered into N-ethylethylenediamine (0.22 mL, 2.05 mmol). The mixture was stirred for 3 hours at room temperature. The solvent was removed in vacuo and the residue was column chromatographed on alumina with CHCl$_3$ and CHCl$_3$/MeOH to give 0.25 g (39%) of biotinamine,

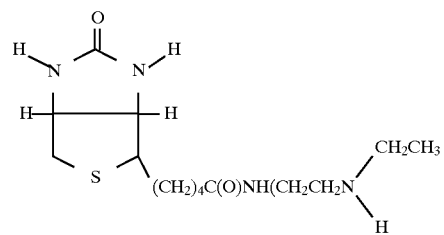

$^1$H NMR (CDCl$_3$+D$_2$O): δ1.09 (t, 3H), 1.35–1.85 (m, 6H), 2.22 (t, 2H), 2.55–2.97 (m, 5H), 3.05–3.5 (m, 4H), 4.22–4.37 (m, 1H), 4.43–4.57 (m, 1H).

The biotinamine (143 mg, 045 mmol) was dissolved in a mixture of DMSO (1 mL) and acetone (1 mL) at 0°–5° C.

To this solution was added a mixture of carbon disulfide (27 µL) and acetone (30 µL) and, after stirring for 10 minutes at 0°–5° C., a solution of NaOH (19 mg) in water (91 µL) was added and the mixture was stirred at 0°–5° C. for 20 minutes. Acetone was added to precipitate biotindithiocarbamate,

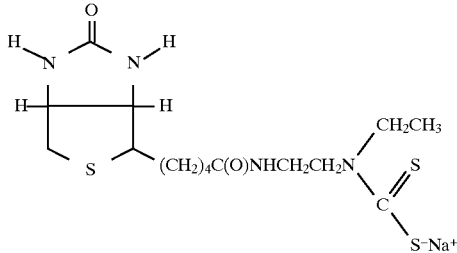

which was separated by filtration and washed with ethyl ether. The product was dried under vacuum and stored under argon. The biotindithiocarbamate can also be used for determination of lead and other heavy metals.

EXAMPLE 14

Determination of Copper Using Biotin Dithiocarbamate Conjugate (Reagent 5)

A stock solution of $9.2 \times 10^{-5}$M biotin dithiocarbamate conjugate was prepared in $1.0 \times 10^4$M NaOH. An aliquot of this solution (44 µl) was added to 2 ml of 0.2N NaCl, 0.05% Tween-20 (ICN) and stirred (R1). R2 consisted of a 2 mg/ml suspension of 60 µg/mg avidin latex particles (Example 11) in 0.9% (w/v) NaCl, and 0.1% Tween-20.

The assay of copper was done on the RA-XT at 37° C. using zero-order quadratic rate chemistry parameters.

RA-XT parameters:

R1 320 µl

R2 80 µl

Sample volume 4 µl

Filter 600 nm

Delay time 15 seconds

R2 delay 1 minute

Figure 2:
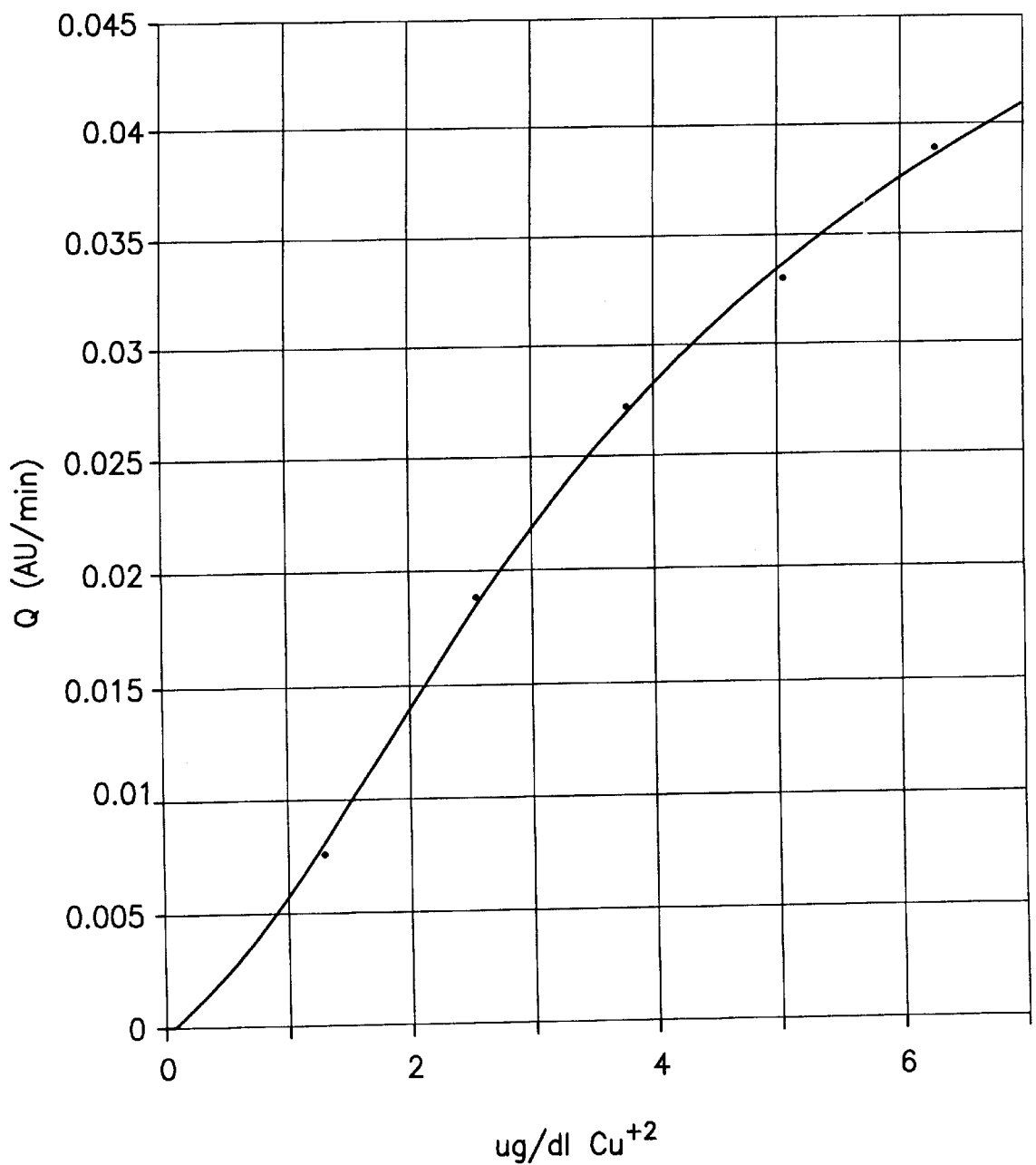

Aqueous samples were prepared to contain $0.0–1.0 \times 10^{-4}$M copper. The samples were diluted 100 fold on the RA-XT to yield final concentrations of 0.0–6.4 µg/dl copper. The Q rate (AU/min) reported by the instrument is tabulated in Table 7 and was used to plot the response curve shown in FIG. 2.

TABLE 7

Copper response on RAXT

| [$Cu^{2+}$], µg/dl | Q(AU/min) |
|---|---|
| 0 | −0.0008 |
| 1.27 | 0.0078 |
| 2.54 | 0.0186 |
| 3.81 | 0.0269 |
| 5.08 | 0.0329 |
| 6.35 | 0.0389 |

What is claimed is:

1. A method for determining the amount of a polyvalent metal ion in a liquid matrix using a sandwich aggregation assay, comprising:

(a) contacting the polyvalent metal ion with a reagent comprising a chelating agent, wherein the chelating agent is capable of forming at least a 2:1 stoichiometric ratio complex of chelating agent to polyvalent metal ion;

(b) linking the chelating agent to a carrier in the liquid matrix wherein a plurality of carriers linked to complexed chelating agents aggregate, thereby causing an increase in light absorbance which is proportional to the concentration of the polyvalent metal ions in the liquid matrix; and (c) measuring the resulting aggregation in the liquid matrix as a function of the amount of the polyvalent metal ion present in the liquid matrix.

2. The method of claim 1, wherein the polyvalent metal ion is selected from the group consisting of lead, copper, cadmium, cobalt, calcium chromium, iron, aluminum, manganese, molybdenum, mercury, nickel, uranium, vanadium, zinc, and magnesium.

3. The method of claim 1, wherein the polyvalent metal ion is a heavy metal selected from the group consisting of lead, cadmium and mercury.

4. The method of claim 3, wherein the ion is lead.

5. The method of claim 1, wherein the resulting aggregation is measured by measuring the light absorbance or light scattering of the reaction mixture.

6. The method of claim 1, wherein the carrier is at least one selected from the group consisting of latex particles, fine pigments, oxide particles, and sulfates.

7. The method of claim 1, wherein the mean particle size of the carriers is between about 0.001 microns and about 10 microns.

8. The method of claim 1, wherein the carriers are covalently linked to the chelating agent.

9. The method of claim 1, wherein the carriers are non-covalently linked to the chelating agent.

10. The method of claim 1, wherein the chelating agent is selected from the group consisting of mercaptoamides, mercaptothioamides, mercaptans, mercaptoamines, mercaptothiones, aminothiones, thiohydroxamic acids, hydroxypyridinethiones, aminothiophenols, aminophenols, and dithiocarbamates.

11. The method of claim 1, wherein the chelating agent is linked to the carrier when the chelating agent complexes with the polyvalent metal ion.

12. A method for determining the amount of a polyvalent metal ion in a liquid matrix using a sandwich aggregation assay, comprising:

(a) contacting the polyvalent metal ion with a reagent comprising a chelating agent linked to a carrier, wherein the chelating agent is capable of forming at least a 2:1 stoichiometric ratio complex of chelating agent to polyvalent metal ion, wherein upon complexation of the chelating agent with the polyvalent metal ion, a plurality of carriers linked to complexed chelating agents aggregate, thereby causing an increase in light absorbance which is proportional to the concentration of the polyvalent metal ions in the liquid matrix; and (b) measuring the resulting aggregation in the liquid matrix as a function of the amount of the polyvalent metal ion present in the liquid matrix.

13. The method of claim 12, wherein the polyvalent metal ion is selected from the group consisting of lead, copper, cadmium, cobalt, calcium, chromium, iron, aluminum, manganese, molybdenum, mercury, nickel, uranium, vanadium, zinc, and magnesium.

14. The method of claim 13, wherein the ion is lead.

15. The method of claim 12, wherein the resulting aggregation is measured by the measuring light absorbance or light scattering of the reaction mixture.

16. The method of claim 12, wherein the carrier is at least one selected from the group consisting of latex particles, fine pigments, oxide particles, and sulfates.

17. The method of claim 12, wherein the carriers are covalently linked to the chelating agent.

18. The method of claim 12, wherein the carriers are noncovalently linked to the chelating agent.

19. The method of claim 12, wherein the chelating agent is selected from the group consisting of mercaptoamides, mercaptothioamides, mercaptans, mercaptoamines, mercaptothiones, aminothiones, thiohydroxamic acids, hydroxypyridinethiones, aminothiophenols, aminophenols, and dithiocarbamates.

20. A method for determining the amount of a polyvalent metal ion in a matrix using a sandwich aggregation assay, comprising:

(a) contacting the polyvalent metal ion with a reagent comprising a conjugate of a ligand and a chelating agent capable of forming at least a 2:1 stoichiometric ratio complex of chelating agent to polyvalent metal ion, (b) contacting the complexed chelating agent with a carrier in the liquid matrix, said carrier being linked to a specific binding partner for said ligand, whereby a plurality of said carriers bind to the complexed chelating agent through the interaction of the ligand and the binding partner and aggregate in liquid matrix, thereby causing an increase in light absorbance which is proportional to the concentration of the polyvalent metal ions in the liquid matrix; and (c) measuring the resulting aggregation in the liquid matrix as a function of the amount of the polyvalent metal ion present in the liquid matrix.

21. The method of claim 20, wherein the polyvalent metal ion is selected from the group consisting of lead, copper, cadmium, cobalt, calcium, chromium, iron, aluminum, manganese, molybdenum, mercury, nickel, uranium, vanadium, zinc, and magnesium.

22. The method of claim 21, wherein the ion is lead.

23. The method of claim 20, wherein the resulting aggregation is measured by measuring the light absorbance or light scattering of the reaction mixture.

24. The method of claim 20, wherein the carrier is at least one selected from the group consisting of latex particles, fine pigments, oxide particles, and sulfates.

25. The method of claim 20, wherein the ligand/specific binding partner pair is selected from the group consisting of biotin/avidin and haptens/anti-hapten antibodies.

26. The method of claim 20, wherein the carriers are covalently linked to the specific binding partner.

27. The method of claim 20, wherein the carriers are non-covalently adsorbed to the specific binding partner.

28. The method of claim 20, wherein the chelating agent is selected from the group consisting of mercaptoamides, mercaptothioamides, mercaptans, mercaptoamines, mercaptothiones, aminothiones, thiohydroxamic acids, hydroxypyridinethiones, aminothiophenols, aminophenols, and dithiocarbamates.

29. A method for determining the amount of lead ions in a liquid matrix using a sandwich aggregation assay, comprising:

(a) contacting the lead ions with a reagent comprising a chelating agent, wherein the chelating agent is capable of forming at least a 2:1 stoichiometric ratio complex of chelating agent to lead ions;

(b) linking the chelating agent to a carrier in the liquid matrix wherein a plurality of carriers linked to complexed chelating agents aggregate, thereby causing an increase in light absorbance which is proportional to the concentration of the lead ions in the liquid matrix; and (c) measuring the resulting aggregation in the liquid matrix as a function of the amount of the lead ions present in the liquid matrix.

30. The method of claim 29, wherein the resulting aggregation is measured by measuring the light absorbance or light scattering of the reaction mixture.

31. The method of claim 29, wherein the carrier is at least one selected from the group consisting of latex particles, fine pigments, oxide particles, and sulfates.

32. The method of claim 29, wherein the chelating agent is selected from the group consisting of mercaptoamides, mercaptothioamides, mercaptans, mercaptoamines, mercaptothiones, aminothiones, thiohydroxamic acids, hydroxypyridinethiones, aminothiophenols, aminophenols, and dithiocarbamates.

33. The method of claim 29, wherein the reagent comprises (i) a conjugate of said chelating agent with biotin or a hapten, and (ii) carriers to which is linked avidin or an anti-hapten antibody, respectively.

34. The method of claim 29, wherein the chelating agent is linked to the carrier when the chelating agent complexes with the lead ions.

35. A test composition for determining the amount of a polyvalent metal ion in a liquid matrix using a sandwich aggregation assay, consisting essentially of:

(1) a chelating agent capable of forming at least a 2:1 stoichiometric ratio complex of chelating agent to polyvalent metal ion, and (2) carriers for the chelating agent, wherein said chelating agent:

(a) is linked to said carriers, or (b) is in the form of a conjugate with a ligand, and a specific binding partner for said ligand is linked to said carriers;

wherein, upon complexation of the chelating agent with the polyvalent metal ion, the carriers linked to the complexed chelating agents are characterized by the ability to aggregate, thereby causing an increase in light absorbance which is proportional to the concentration of the polyvalent metal ion in the liquid matrix.

36. The test composition of claim 35, wherein the polyvalent metal ion is selected from the group consisting of lead, copper, cadmium, cobalt, calcium, chromium, iron, aluminum, manganese, molybdenum, mercury, nickel, uranium, vanadium, zinc, and magnesium.

37. The test composition of claim 35, wherein the ion is a heavy metal selected from the group consisting of lead, cadmium and mercury.

38. The test composition of claim 37, wherein the ion is lead.

39. The test composition of claim 35, wherein the carrier is at least one selected from the group consisting of latex particles, fine pigments, oxide particles, and sulfates.

40. The test composition of claim 35, wherein the mean particle size of the carriers is between about 0.001 microns and about 10 microns.

41. The test composition of claim 35, wherein the chelating agent is selected from the group consisting of mercaptoamides, mercaptothioamides, mercaptans, mercaptoamines, mercaptothiones, aminothiones, thiohydroxamic acids, hydroxypyridinethiones, aminothiophenols, aminophenols, and dithiocarbamates.

42. The composition of claim 35, wherein the carrier is linked to the chelating agent.

43. The composition of claim 35, wherein the chelating agent is in the form of a conjugate with a ligand and the carrier is linked to a specific binding partner for said ligand.

44. The method of claim 1, wherein the selectivity of the assay is enhanced by using suitable masking agents.

\* \* \* \* \*